United States Patent
Tang et al.

(10) Patent No.: US 8,841,292 B2
(45) Date of Patent: Sep. 23, 2014

(54) INDUCED HYPOTHERMIA

(75) Inventors: Wanchun Tang, Palm Desert, CA (US); Shijie Sun, Palm Desert, CA (US)

(73) Assignee: Weil Institute of Critical Care Medicine, Rancho Mirage, CA (US)

( * ) Notice: Subject to any disclaimer, the term of this patent is extended or adjusted under 35 U.S.C. 154(b) by 140 days.

(21) Appl. No.: 13/212,758

(22) Filed: Aug. 18, 2011

(65) Prior Publication Data
US 2013/0045971 A1    Feb. 21, 2013

(51) Int. Cl.
*A61K 31/54*    (2006.01)

(52) U.S. Cl.
USPC ..................................................... 514/222.8

(58) Field of Classification Search
None
See application file for complete search history.

(56) References Cited

FOREIGN PATENT DOCUMENTS

WO    WO 2010015260 A2 *    2/2010

OTHER PUBLICATIONS

Sun et al., Pharmacologically induced hypothermia with cannabinoid receptor agonist WIN55, 212-2 after cardiopulmonary resuscitation, Critical Care Medicine (2010), 38(12), 2282-2286.*
The Hypothermia after Cardiac Arrest Study Group, N. Engl. J. Med., vol. 346, No. 8, 549-556, Feb. 21, 2013.*
STN document No. 152:255274.*
STN document No. 155:1501.*
The Hypothermia after Cardiac Arrest Study Group, N. Engl. J. Med., vol. 346, No. 8, 549-556, Feb. 21, 2002 ("The Hypothermia after Cardiac Arrest Study Group").*
STN document No. 152:255274, Feb. 11, 2010.*
STN document No. 155:1501, Nov. 22, 2010.*

* cited by examiner

*Primary Examiner* — Sreenivasan Padmanabhan
*Assistant Examiner* — Svetlana M Ivanova
(74) *Attorney, Agent, or Firm* — Lawrence S. Cohen; Timothy T. Tyson

(57) ABSTRACT

Sudden cardiac arrest is treated by reducing blood temperature from about 37° C. to 33° C., following resuscitation, by injecting hypothermia inducing drugs such as a cannabinoid type into the patient's body, preferably in combination with physical surface body cooling.

2 Claims, 1 Drawing Sheet

INDUCED HYPOTHERMIA

BACKGROUND OF THE INVENTION

During the past decade, clinical studies have been conducted to actively reduce the blood temperature of victims of sudden cardiac arrest, following resuscitation. These studies have demonstrated that rapidly reducing blood temperature to 32°-34° C. following resuscitation, significantly improves survival. Currently available therapeutic hypothermia techniques are based on physical cooling, as by placing the patient in a bath of cold water with ice. This is usually available only in hospitals because of the large physical dimensions and complexity of use. Such physical cooling requires nearly 8 hours to achieve the target cooling temperature in clinical practice.

SUMMARY OF THE INVENTION

It can be difficult to rapidly lower body temperature. This is because the body tends to maintain a constant "core" temperature such as 37° C. (98.6° F.) through feedback pathway regulating centers in the hypothalamus. Applicant reduces body temperature by blocking temperature regulating centers. This is done by the early application of pharmacological agents, alone or in combination with physical cooling.

One effective pharmaceutical agent is cannabinoid. When it was injected intramuscularly (into a rat or pig), it produced hypothermia, reducing the body temperature in a rat from 37° C. to 34° C. during a period of 60 to 180 minutes, A similar result was obtained in injection of cannabinoid in a pig of 60 kg body weight.

The novel features of the invention are set forth with particularity in the appended claims. The invention will be best understood from the following description when read in conjunction with the accompanying drawings.

DESCRIPTION OF THE PREFERRED EMBODIMENT

Figure 1:
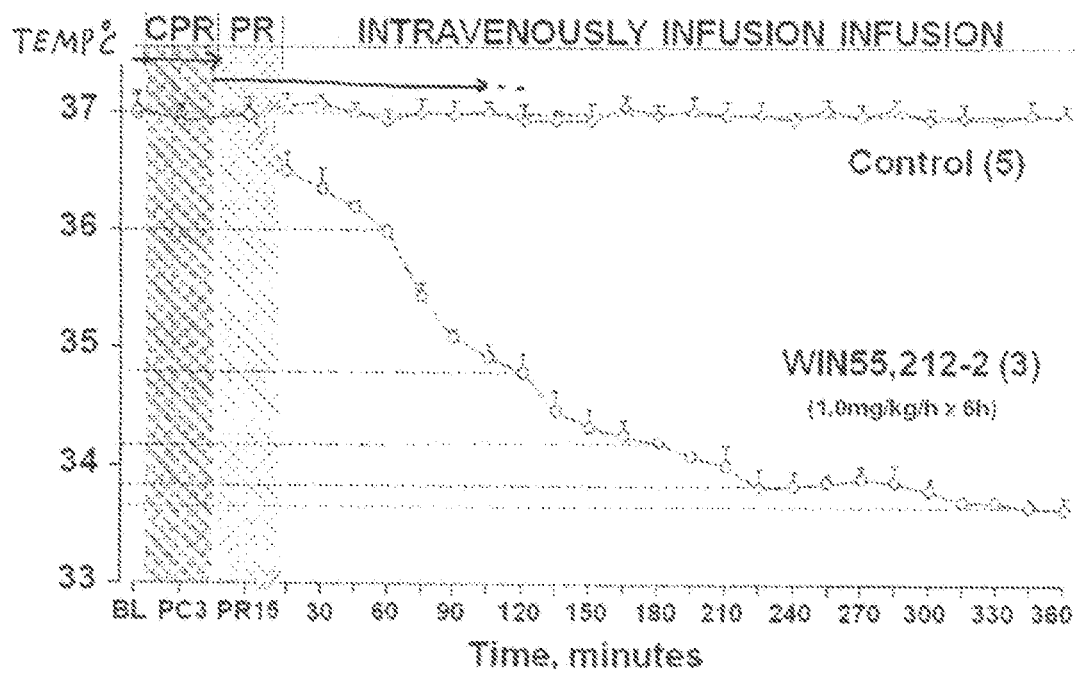
FIG. 1 is a chart showing the average body temperature of five control subjects (rats) not receiving a pharmacological drug after CPR (cardiopulmonary resuscitation), compared to three subjects who received injections of WIN 55.212-2.

Each year in the United States, approximately 350,000 victims suffer sudden cardiac arrest outside of a hospital. However, the outcomes of current cardiopulmonary resuscitation (CPR) are disappointing, as they yield a functional survival rate of only 1.4 to 5%. During the last decade, clinical studies have demonstrated that actively reducing the blood temperature to 32-34° C. (89.6° F.-93.2° F.) following resuscitation significantly improved neurologically favorable survival. The most recent studies further demonstrated that both early application of hypothermia and rapid achievement of target cooling temperature were the key factors for improving neurological outcome and survival. Unfortunately, currently available therapeutic hypothermia techniques are all based on the physical cooling principle. These techniques are either less effective or limited for in hospital use because of the physical dimension and complexity of use. As a result, only <10% of these victims receive this potentially lifesaving therapy and it requires nearly 8 hours to achieve target cooling temperature in clinical practice. Accordingly, current cooling techniques can help save only a small fraction of the lives that would be possible if a more effective cooling technique could be implemented. Such cooling would be desirable for cardiac arrest, strokes, and any other conditions in which body cooling would be useful.

The human body normally maintains a constant "core" temperature by balancing heat production against heat loss. This process is regulated almost entirely by nervous feedback mechanisms through temperature regulating centers located in the hypothalamus. If the feedback pathway is blocked or the temperature regulating centers are prohibited from functioning pharmacologically, body temperature could be reduced rapidly by both reduced heat production and increased heat loss. In our early preliminary studies, administration of temperature regulating center prohibiting agent during CPR, reduced blood temperature from 37° C. to 34° C. within 3 hours. This novel approach opens a new option for inducing therapeutic hypothermia. Early application of hypothermia and rapid achievement of target cooling temperature could be practically achieved by early application of the pharmacological agent(s) alone or in combination with physical cooling. The goals of the proposed studies are (1) to investigate the effects of a pharmacological agent that acts through the temperature regulating centers on blood temperature and outcomes of CPR, and (2) to investigate the effects of the combination of this agent and body surface cooling on blood temperature and outcomes of CPR.

Applicant investigates the effects of WIN55, 212-2, which is the cannabinoid $CB_1/CB_2$ receptor agonist when administered immediately following resuscitation on blood temperature, post resuscitation myocardial and cerebral functions, and duration of survival in our porcine model of CPR. We hypothesize that when WIN55, 212-2 is administered immediately following resuscitation, it will rapidly achieve the target blood temperature (34° C., <3 hours). These will therefore improve post resuscitation myocardial and cerebral functions, and duration of survival. We further hypothesized that the beneficial effects of WIN55, 212-2 will be blocked by pre-treatment of the selective $CB_1$ antagonist.

Applicant investigates the effects of WIN55, 212-2 in combination with physical surface body cooling when applied immediately following resuscitation, on blood temperature, post resuscitation myocardial and cerebral functions, and duration of survival in our porcine model of CPR. We hypothesize that when WIN55, 212-2 is administered in combination with physical surface body cooling immediately following resuscitation, the combination will further reduce the duration for achieving target blood temperature (<1 hour). It will therefore further improve post resuscitation myocardial and cerebral functions, and duration of survival.

We start from the concept that therapeutic hypothermia could be induced by pharmacological means and apply this knowledge to the setting of cardiac arrest and resuscitation. Such studies improve understanding of how to regulate temperature control pharmacologically in the setting of cardiac arrest. This research is also transnational in nature since the results of the proposed studies will potentially lead to a novel and more effective means to produce therapeutic hypothermia and lead to an improvement in survival following systems that suggest sudden death.

In the United States, approximately one half of the 2 million deaths each year are due to cardiovascular disease. Of these deaths, approximately one-third or 350,000 occur suddenly and outside of the hospital. Thus, each minute, one person is the victim of "sudden (cardiac) death" in the United States, and almost one half of the victims are under 65 years of age. Current advanced cardiac life support therapies with CPR, defibrillation, and medications save less than 5% of victims despite the substantial evidence that many of these lives could be saved with improved resuscitation protocols, including the expanded use of hypothermia. Even more alarming is that the survival rates of these victims have improved little over the last 50 years.

Hypothermia induced by physical cooling for the treatment of cardiac arrest is not a new therapy. However, its use in cardiac arrest patients was re-popularized by two landmark clinical studies in 2002. Clinical cooling to 33° C. in comatose victims of cardiac arrest who achieved return of spontaneous circulation (ROSC) after ventricular fibrillation was noted to have an absolute improvement in the rate of neurologically favorable survival of 16%. In animal models of cardiac arrest, early application of hypothermia and rapid achievement of target temperature have been shown to significantly improve survival and long-term neurologic outcome. On the basis of these clinical and laboratory studies, the American Heart Association recommended the use of hypothermia for routine management of cardiac arrest patients following initial successful resuscitation.

Unfortunately, currently available therapeutic hypothermia techniques are uniformly based on the physical cooling principle. These techniques are either less effective or limited for in-hospital use because of the physical dimension and complexity of application. At the present time, the emergency rescuers have no practical means to rapidly cool a patient in the field while the patient is in cardiac arrest. Current methods such as cold blankets and chilled intravenous saline are easy to implement but with limited effectiveness. By contrast, rapid methods such as cooling via cardiopulmonary bypass are highly effective at cooling but practically very difficult to implement in the pre-hospital setting. As the result, the routine use of hypothermia has been slow to disseminate into clinical practice and many pre-hospital emergency systems and hospitals today are still not routinely using hypothermia. While the adoption of this therapy has led to improved outcomes from cardiac arrest at multiple hospitals worldwide, the time from arrest to target temperature achievement is still on the order of hours.

The human body maintains a constant "core" temperature by balancing heat production against heat loss. This process is regulated almost entirely by nervous system feedback mechanisms through temperature regulating centers located in the hypothalamus. The thermoregulatory system in humans comprises warm- and cold-sensitive neurons located in the central and peripheral nervous system. The thermosensitive neurons in the preoptic anterior hypothalamus (POA) receive signals from both the peripheral sensory neurons (reacting to environmental changes) and the peripheral deep-body sensors (reacting to changes in core temperature) and regulate the heat production or loss accordingly. During the last 2 decades, laboratory studies have demonstrated that the body temperature regulating system could be influenced by a number of pharmacological agents acting through different mechanisms. These agents include cannabinoid agonist, cholecystokinin octapeptide, antipyretic/anti-inflammatory drugs, neuroleptic/antimaniacal/antidepressant drugs, capsaicin-type drugs, neurotension, and opioid receptor agonists. These basic studies, though not related directly to therapeutic hypothermia, provided a strong theoretic foundation that in settings of CPR, early and rapid hypothermia could be induced by pharmacological means. This concept will provide a new, effective and easy to use option for the widespread use of live saving hypothermia during and following CPR.

Among the agents discussed above, cannabinoids produced the most profound hypothermia in normal rats through the activation of central $CB_1$ receptors. WIN 55, 212-2, the nonselective cannabinoid $CB_1/CB_2$ receptor agonist, produced hypothermia in a dose-dependent manner when injected intramuscularly. The body temperature reduced from 37 to 34° C., 60 to 180 mins post injection and the hypothermia was maintained up to 5 hours. The effect was completely blocked by the selective $CB_1$ antagonist.

Figure 2:
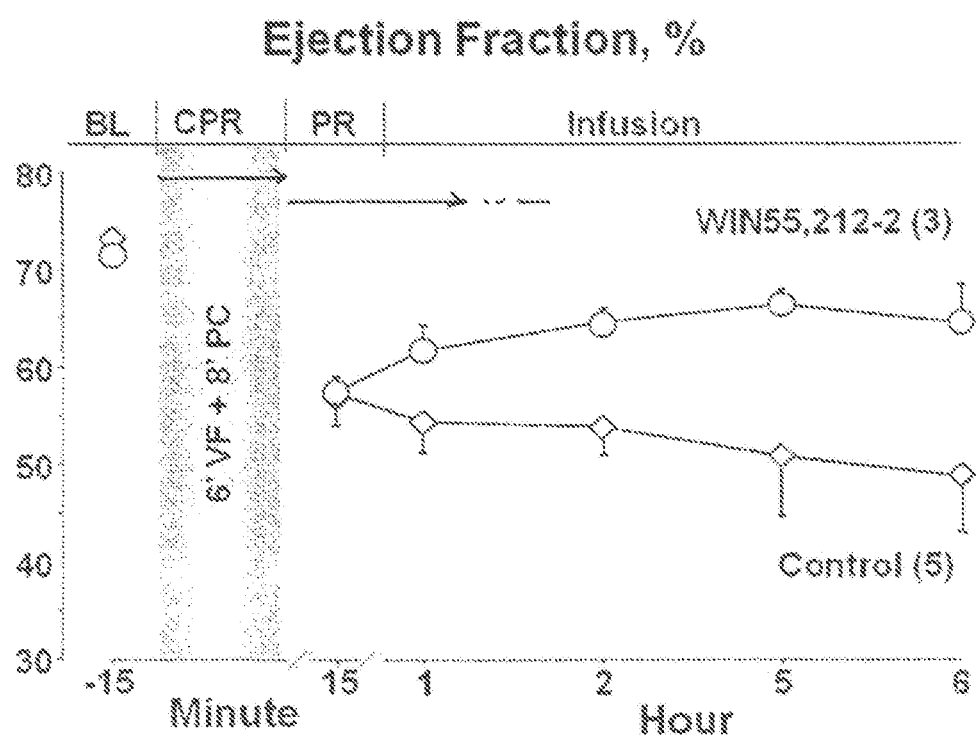
FIG. 2 is a chart showing the ejection fraction vs. time for the two groups of subjects of FIG. 1.

The effects of WIN 55, 212-2 were investigated initially in our rat model of cardiac arrest and resuscitation. WIN 55, 212-2 was selected based on the following reasons: 1) the described hypothermia effect of $CB_1$ agonist is convincing and well documented, 2) it is highly selective for cannabinoid receptors and interacts negligibly with other neurotransmitter and ion channels, 3) it is expressed in the thermoregulatory areas of the central nervous system and therefore decreases the body temperature via central mechanism, 4) It has been shown to be neuroprotective. Ventricular fibrillation was induced and untreated for 6 mins and followed by 8 mins of CPR. Resuscitation was then attempted with defibrillation. WIN 55, 212-2 was infused intravenously 10 mins after resuscitation in a dose of 1 mg/kg/hour and continued for 6 hours. The body temperature decreased from 37 to 34° C. within 4 hours after infusion (FIG. 1). All animals that received WIN 55, 212-2 survived for more than 72 hours with minimal neurological deficits. The post resuscitation myocardial function was significantly better than the controls (FIG. 2). Similar results were observed in a study in our porcine model of CPR. We therefore demonstrated the feasibility that therapeutic hypothermia could be induced pharmacologically in settings of CPR without compromising the outcomes of CPR.

It is likely that our new concept of pharmacologically induced hypothermia will change the direction of current laboratory and clinical studies and provide a new, easy and effective option for early and rapid induction of live-saving therapeutic hypothermia during and following resuscitation. Specifically:

1. To the best of our knowledge, this proposal and our early preliminary studies are the very first to apply the concept that the temperature regulating-centers could be manipulated pharmacologically into the practice of therapeutic hypothermia in settings of cardiopulmonary resuscitation.

2. Therapeutic hypothermia has been demonstrated as a live-saving therapy following resuscitation from cardiac arrest. It is recommended as a standard care by American Heart Association CPR guidelines since 2005. However, the widespread use of this live-saving therapy is limited because all current available cooling techniques are based on the physical cooling principle. These techniques are either less effective or limited to in-hospital use because of the physical dimension and complexity of application. Pharmacologically induced hypothermia alone or in combination with physical cooling provide the new options for early and rapid induction of live-saving therapeutic hypothermia. Because of the effectiveness and easy application, hypothermia will be adopted by more emergency care providers. It will greatly change the current clinical practice and ultimately, save more lives.

3. The application of pharmacologically induced hypothermia is not only limited in settings of CPR, but this concept could be applied to other settings such as trauma, brain injury and stroke where the beneficial effects of hypothermia have been demonstrated.

A porcine model of cardiac arrest and resuscitation in domestic pigs, weighing between 40±2 kg, is utilized for a proposed study that applicant is conducting. The porcine model is selected because (1) it has a large body mass and the timing of reduction in body temperature during hypothermia is close to that of the human. (2) It is an established model for investigation of pharmacological interventions in the setting of CPR; observations on this model have been comparable to those made in human patients. (3) A large animal model facilitates non-invasive measurements of myocardial function by echocardiographic methods, preserving an intact chest wall for conventional CPR, and specifically, precordial compression. (4) Our research team has had extensive experience for more than 20 years with the porcine model, under conditions of cardiac arrest and resuscitation.

Our aims are to investigate the effects of WIN55, 212-2, the cannabinoid $CB_1/CB_2$ receptor agonist, when administered immediately following resuscitation with or without physical surface body cooling on blood temperature, post resuscitation myocardial and cerebral functions, and duration of survival in our porcine model of CPR. We hypothesize that when WIN55, 212-2 is administered immediately following resuscitation, it will rapidly achieve the target blood temperature (34° C., <3 hours), therefore improving post-resuscitation myocardial and cerebral functions, and duration of survival. We further hypothesize that when WIN55, 212-2 is administered in combination with physical surface body cooling, the combination will further reduce the duration for achieving target blood temperature (<1 hour). It will therefore further improve post-resuscitation myocardial and cerebral functions, and duration of survival. Those effects of WIN55, 212-2, however, will be completely blocked by the selective $CB_1$ antagonist, SR141716A.

To test our hypotheses, the independent variables are the WIN55, 212-2 and WIN55, 212-2 with physical surface cooling. The study design is shown in Table 1. The rationale for selecting WIN 55, 212-2 is that the two groups pretreated with either selective $CB_1$ antagonist, SR141716A or selective $CB_2$ antagonist, SR144528 are included to identify the potential mechanism of WIN55, 212-2. All of these agents are commercially available and the doses of these agents have been established in the earlier studies performed in our laboratory.

TABLE 1

Study Design

| Group | Pre-treatment |
| --- | --- |
| WIN55,212-2 | No |
| WIN55,212-2 with cooling blanket | No |
| WIN55,212-2 | CB, antagonist |
| WIN55,212-2 | CB2 antagonist |
| Saline placebo | No |

The primary dependent variables are the time required to achieve target body temperature (34° C.), the severity of post-resuscitation myocardial and cerebral dysfunctions, and the percent of animals surviving at 24, 48, and 72 hours.

Measurements of myocardial systolic and diastolic functions include left ventricular end-systolic and end-diastolic volumes, stroke volumes, ejection fractions, and myocardial performance index. Those measurements are obtained by echocardiographic techniques. Our group has had successful experience with this technique in experimental settings of cardiac arrest and resuscitation.

The neurological deficit score is utilized for evaluating post-resuscitation cerebral function. It consists of level of consciousness, motor and sensory function, respiratory pattern, and behavior. Histopathologic damages of the brain are also evaluated at the conclusion of each study.

In experiments, male domestic pigs, weighing 40±2 kg, are fasted overnight except for free access to water. Anesthesia is initiated by an intramuscular injection of ketamine (20 mg $kg^{-1}$) and completed by an ear vein injection of sodium pentobarbital (30 mg $kg^{-1}$). A cuffed endotracheal tube is advanced into the trachea. Animals are mechanically ventilated with a volume-controlled ventilator (Model MA-1, Puritan-Bennett, Carlsbad, Calif.). End-tidal PC02 is monitored with an infrared analyzer (Model 01R-7101A, Nihon Kohden Corp, Tokyo, Japan). Respiratory frequency is adjusted to maintain $P_{ET}CO_2$ between 35 and 40 mm Hg. Additional doses of sodium pentobarbital (8 mg kg-1) are administered at intervals of one hour to maintain anesthesia.

For the measurement of aortic pressure, a catheter-tipped transducer (SPR-524, Millar Instr. Corp., Houston, Tex.) is advanced from the left femoral artery into the thoracic aorta. A 7-French, pentalumen, thermister-tipped thermodilution catheter is advanced from the left femoral vein and flow-directed into the pulmonary artery. This catheter also provides for the measurements of right atrial pressure through its atrial port and for measurements of cardiac output by the conventional thermodilution method. The thermistor also allows for measurement of core (blood) temperature. A 7-French pacing catheter (EP Technologies, Inc., Mountain View, Calif.) is advanced from the right cephalic vein into the right ventricle until an electrocardiographic current of injury indicates endocardial contact. The catheter is subsequently advanced into the apex of the right ventricle with the aid of image intensification. This catheter serves as an electrode for inducing VF.

The experimental room temperature is maintained constantly at 21+0.20 C with relative humidity of 52±2%. During baseline, the animal blood temperature is maintained at 38+0.1° C. (normal blood temperature for pig) with a cold or warm blanket. Fifteen mins prior to induction of VF, the animals are randomized by the sealed envelope method. The envelope is opened by a technician who prepares the drugs. The investigators are blinded to the randomization. Cardiac arrest is induced with 1 to 2 mA AC delivered to the endocardium of the right ventricle. Mechanical ventilation is discontinued after onset of VF. At the end of a 10 min interval of untreated VF, precordial compression is started with a pneumatic piston-driven chest compressor (Thumper, Model 1000, Michigan Instruments, Grand Rapids, Mich.). Coincident with the start of precordial compression, the animal is mechanically ventilated with a tidal volume of 15 ml $kg^{-1}$ and $FiO_2$ of 1.0. Precordial compression is programmed to provide 100 compressions per min and synchronized to provide a compression/ventilation ratio of 30:2 with equal compression-relaxation intervals, i.e. a 50% duty cycle. The compression force is adjusted to decrease the anterior-posterior diameter of the chest by 25%. After 8 mins of precordial compression, defibrillation is attempted with a 150 J biphasic waveform shock delivered between the right infraclavicular area and the cardiac apex. If an organized cardiac rhythm with mean aortic pressure of more than 60 mm Hg persists for an interval of 5 mins or more, the animal is regarded as successfully resuscitated.

For animals randomized to receive pre-treatment of either CB, or C132 antagonist, either SR141716A (2 mg/kg, Sigma, St. Louis, Mo.) or SR144528 (5 mg/kg, Sigma, St. Louis, Mo.) is administered intravenously 5 mins after resuscitation. WIN 55, 212-2 (1 mg/kg/h, Enzo, Plymouth Meeting, Pa.) is infused 15 mins later and continued for 6 hours. For animals randomized to receive the combination of WIN 55, 212-2 and surface cooling, the animals are covered with a water circling blanket with the circling water temperature of 4° C. (BlankeTrol II, CSZ, Cincinnati, Ohio), coincident with the start of infusion of WIN 55, 212-2. Control animals receive the same volume and duration of saline infusion as experimental animals. Measurements, as defined in Section 3.2.3, are then obtained over an additional 6 hours. After 6 hours of observation, the catheters and electrodes are removed, skin sutures are inserted. The animals are then returned to their cages and observed for 72 hours. Buprenorphine is administered in doses of 0.02 mg kg$^{-1}$ intramuscularly at 6 hour intervals, contingent on the observed activity of the animal. After 72 hours, animals are euthanized by intravenous injection of 150 mg kg$^{-1}$ pentobarbital. Autopsy is routinely performed to document possible injuries to the bony thorax and the thoracic or abdominal viscera during CPR or adverse effects of instrumentation. The brains are harvested for histopathologic evaluation.

Dynamic data, including blood temperature, aortic, right atrial, pulmonary arterial, and left ventricular pressures, myocardial tissue $PO_2$, and $PCO_2$, end-tidal $PCO_2$, together with the electrocardiogram are continuously measured and recorded on a PC-based data acquisition system, supported by CODAS hardware/software by methods as previously described. A total of 16 channels are available for continuous recording at appropriate sampling frequencies for the studies proposed. The CPP is digitally computed and hemodynamic measurements and the electrocardiogram are displayed in real time.

Myocardial function is measured with echocardiographic measurements with the aid of a Philips HD11XE echocardiographic system (Andover, Mass.) using a 5.5/7.5 Hz biplane Doppler transesophageal transducer with 4-way flexure. The operator of the system is blinded to the randomization. Two-dimensional echocardiograph and Doppler measurements are performed. Left ventricular end-systolic and end-diastolic volumes are calculated by the method of discs. From these, ejection fraction and fractional area change are computed using the simplified Simpson's rule. Trans-mitral pulsed-wave Doppler velocities are recorded in the apical four-chamber view. The interval from cessation to onset of mitral inflow is measured. From the five-chamber apical view, aortic flow is recorded using pulsed Doppler. Left ventricular ejection time (ET) is measured from the beginning to end of the aortic flow wave. The myocardial performance index is calculated using the formula (a−b)/b, where a=mitral closure-to-opening interval, b=ET. These are measured at hourly intervals for 6 hours and repeated at 24, 48, and 72 hours. The total number and cumulative frequency of ectopic beats are quantitated for 6 hours or until baseline conditions have been reestablished by software developed by our group.

The neurological deficit score as previously described by us is utilized for evaluating cerebral recovery at 24-hour intervals for a total of 72 hours. The neurological deficit is scored on the basis of level of consciousness from 0 (no observed neurologic deficit) to 400 (death or brain death). It consists of level of consciousness, motor and sensory function, respiratory pattern, and behavior. Two investigators unrelated to the studies measure the score independently and reach agreement. Histopathologic measurements are performed at the conclusion of each experiment. Briefly, after brains are harvested, five coronal sections are made from 2 areas of the hippocampus. Paraffin sections are prepared and stained with hematoxylin and eosin staining. The histopathologic measurements are performed by a pathologist who is blinded to interventions.

Aortic and mixed venous blood gases, hemoglobin and oxyhemoglobin are measured on 200 μL aliquots of blood with a stat profile analyzer (ULTRA C, Nova Biomedical Corporation, Waltham, Mass.) adapted for porcine blood. Arterial blood lactate is measured with a lactic acid analyzer (Model 23L, Yellow Springs Instruments, Yellow Springs, Ohio). These measurements are obtained at 30 mins prior to cardiac arrest, after 7 mins of CPR and at hourly intervals after resuscitation, for a total of 6 hours.

The independent variables are the WIN55, 212-2 and WIN55, 212-2 with physical surface cooling. The primary dependent variables are the time required to achieve target body temperature (34° C.), the severity of post-resuscitation myocardial and cerebral dysfunctions, and the percent of animals surviving at 24, 48, and 72 hours.

For comparison between groups, ANOVA and Scheffe's multi-comparison techniques are used. Comparisons between time-based measurements within each group are performed with ANOVA repeated measurements. When the dependent variable is a categorical variable, including rates of resuscitation, 24, 48, and 72 hour survival, Fisher's exact test will be used.

Data on which to base sample size are as yet limited and based largely on the preliminary studies. Two key dependent variables, namely, left ventricular ejection fraction and neurological deficit score are believed to be of predominant import. In our previous studies on pigs, cardiac arrest of 10 min reduced the left ventricular ejection fraction from 65±2 to 42±5%. The neurological deficit score of such animals was 280±16 at 24 hours after resuscitation. Based on these earlier experiments, a 30% or greater change in these variables is of significance. Accordingly, a sample size of 15 animals per group would provide a power of 0.80 with an a level of 0.05.

The one-directional stopping rule is also utilized for this study. Experiments are therefore randomized into blocks of 5 animals for each group. At the end of each block, if a significance level of 0.05 or greater is reached with the primary dependent variables, including measurements of myocardial, cerebral function and duration of survival between groups, no additional experiments are intended. However, if no significant differences are detected at the end of each block, a power analysis is performed and additional animals are enrolled or the block is abandoned.

Healthy male Yorkshire-X domestic pigs (*Sus scrofa*) aged 5-6 months, weighing between 40±2 kg, are supplied by a single source breeder who has consistently supplied healthy animals of relatively uniform age and weight. A total of 75 animals is projected for the proposed study.

The porcine model is selected because it is an excellent and widely used sub-primate model for cardiovascular studies of clinical interest and especially CPR, as detailed above. The chest configuration of the pig resembles that of the human chest as compared to the keel shape of canine models in which precordial compression is less effective. The heart and vascular anatomy of the pig is more like that of the human than other sub-primate species. Our earlier studies have allowed us to define normal ranges for porcine blood chemistry and hemodynamic parameters and these correspond closely to those of human subjects.

The animals are acclimated to our facility 5-7 days prior to experiment. Our animal facility fully complies with the principles in the "Guide for the Care and Use of Laboratory Animals" and is fully accredited by the American Association for Accreditation of Laboratory Animal Care (AAALAC) and the NIH. The laboratory is also certified by the US Department of Agriculture and by the Riverside County, California Health Department.

The animals are sedated with ketamine 20 mg/kg for pre-anesthesia. They are placed on a V-shaped board and restrained on all 4 extremities. Anesthesia is induced (30 mg/kg) and maintained (8 mg/kg) with sodium pentobarbital. Post-operative analgesia is maintained with Buprenorphine (0.02 mg/kg).

Euthanasia is by lethal injection of sodium pentobarbital of 150 mg/kg. This is consistent with the recommendations of the American Veterinary Medical Association.

Applicant's investigation shows that the injection of a pharmacological drug such as cannabinoid $CB_1/CB_2$ immediately following resuscitation, significantly increases the survival rate, especially when physical cooling is also applied.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method of inducing hypothermia and improving post-resuscitation outcome in a patient who has undergone sudden cardiac arrest and who has been resuscitated, comprising:

physically cooling the patient by applying a cold object to the outside of the skin of the patient;

in combination with the physical cooling, injecting the patient with cannabinoid WIN 55, 212-2 that blocks feedback in the patient's nervous system so the body does not react to a body temperature drop by increasing the production of body heat.

2. A method of inducing hypothermia and improving post-resuscitation outcome in a patient that is a mammal and that has undergone a trauma wherein hypothermia has been shown to be beneficial, comprising:

applying physical cooling to the outside of the patient in combination with the physical cooling injecting the patient with cannabinoid WIN 55, 212-2 that blocks nervous system feedback of the hypothalamus, so the body does not react to a body temperature drop by increasing the production of body heat.

* * * * *